United States Patent
Kanai et al.

(10) Patent No.: US 10,941,394 B2
(45) Date of Patent: Mar. 9, 2021

(54) DEVICE FOR MANIPULATING MAGNETIC PARTICLES AND METHOD FOR MANIPULATING MAGNETIC PARTICLES

(71) Applicant: SHIMADZU CORPORATION, Kyoto (JP)

(72) Inventors: Masaki Kanai, Kyoto (JP); Tetsuo Ohashi, Kyoto (JP); Takahiro Nishimoto, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 853 days.

(21) Appl. No.: 15/543,425

(22) PCT Filed: Jan. 15, 2015

(86) PCT No.: PCT/JP2015/050967
§ 371 (c)(1),
(2) Date: Dec. 13, 2017

(87) PCT Pub. No.: WO2016/113883
PCT Pub. Date: Jul. 21, 2016

(65) Prior Publication Data
US 2018/0112207 A1 Apr. 26, 2018

(51) Int. Cl.
*B01L 3/00* (2006.01)
*C12N 15/10* (2006.01)
(Continued)

(52) U.S. Cl.
CPC .......... *C12N 15/1013* (2013.01); *B01L 3/502* (2013.01); *B03C 1/01* (2013.01); *B03C 1/0332* (2013.01); *B03C 1/288* (2013.01); *B03C 1/30* (2013.01); *C07K 1/14* (2013.01); *C07K 16/00* (2013.01); *B01L 2200/0631* (2013.01); *B01L 2200/0647* (2013.01); *B01L 2200/0673* (2013.01); *B01L 2300/0832* (2013.01);
(Continued)

(58) Field of Classification Search
CPC ....... B01L 2400/043; B01L 2200/0631; B01L 2200/0668
USPC ................................. 422/529, 549, 547, 559
See application file for complete search history.

(56) References Cited

U.S. PATENT DOCUMENTS 5,736,033 A * 4/1998 Coleman ................ B01D 21/24
210/122
6,509,193 B1 1/2003 Tajima
(Continued)

FOREIGN PATENT DOCUMENTS

WO 97/44671 A1 11/1997

*Primary Examiner* — Natalia Levkovich
(74) *Attorney, Agent, or Firm* — Sughrue Mion, PLLC

(57) ABSTRACT

A device for manipulating magnetic particles includes a gelled medium layer and liquid layers alternately stacked in a tubular container along a longitudinal direction of the container. A magnetic particle movement portion for moving magnetic particles exists along an inner wall surface of the container, and the magnetic particle movement portion extends along the longitudinal direction of the container. At a portion where the gelled medium layer is loaded, the cross-sectional shape of the container inner wall in a plane perpendicular to the longitudinal direction of the container is non-circular, and the shape of the magnetic particle movement portion in the cross section is a curved shape or an angular shape.

4 Claims, 4 Drawing Sheets

(51) Int. Cl.
*B03C 1/30* (2006.01)
*B03C 1/01* (2006.01)
*B03C 1/033* (2006.01)
*B03C 1/28* (2006.01)
*C07K 1/14* (2006.01)
*C07K 16/00* (2006.01)

(52) U.S. Cl.
CPC . *B01L 2300/0838* (2013.01); *B01L 2400/043* (2013.01); *B03C 2201/18* (2013.01); *B03C 2201/26* (2013.01)

(56) References Cited

U.S. PATENT DOCUMENTS

2013/0273552 A1 10/2013 Ohashi
2017/0067923 A1 3/2017 Ohashi

* cited by examiner

DEVICE FOR MANIPULATING MAGNETIC PARTICLES AND METHOD FOR MANIPULATING MAGNETIC PARTICLES

CROSS REFERENCE TO RELATED APPLICATIONS

This application is a National Stage of International Application No. PCT/JP2015/050967 filed Jan. 15, 2015, the contents of all of which are incorporated herein by reference in their entirety.

TECHNICAL FIELD

The present invention relates to a device for manipulating magnetic particles and a method for manipulating magnetic particles for performing chemical operations such as separation, extraction, purification and reaction of a target substance.

BACKGROUND ART

In medical inspection, management on safety and sanitation of food, monitoring for environmental conservation, and so on, extraction of a target substance from a sample containing a variety of foreign substances is required for detection and reaction of the target substance. For example, in medical inspection, it is necessary to detect, identify and quantitatively determine a nucleic acid, a protein, a sugar, a lipid, a bacterium, a virus, a radioactive substance or the like which is contained in a biological sample separated and acquired from an animal or a plant, such as blood, serum, cells, urine or feces. In these inspections, it may be required to separate and purify a target substance for eliminating adverse effects such as a background ascribable to foreign substances.

A method for separating and purifying a target substance in a sample using magnetic particles composed of a magnetic substance with a particle size of about 0.5 μm to ten-odd μm, the surface of which has a chemical affinity with the target substance and a molecule recognition function, has been developed and put into practical use. In this method, a target substance is immobilized on the surfaces of magnetic particles, followed by repeatedly carrying out a process in which the magnetic particles are separated and recovered from a liquid phase by magnetic field manipulation, the recovered magnetic particles are dispersed in a liquid phase such as a washing liquid as necessary, and the magnetic particles are separated and recovered from the liquid phase. Thereafter, the magnetic particles are dispersed in an elution liquid, so that the target substance immobilized on the magnetic particles is released in the elution liquid to recover the target substance in the elution liquid. The method is advantageous for automation of chemical extraction and purification because a target substance can be recovered by a magnet due to use of magnetic particles.

Magnetic particles capable of selectively immobilizing a target substance are commercially available as a part of a separation and purification kit. In the kit, a plurality of reagents are contained in separate containers, and in use of the kit, a user isolates and dispenses reagents using a pipette etc. An apparatus for automating such pipette manipulation and magnetic field manipulation is also commercially available (Patent Document 1). As an alternative to pipette manipulation, a method has been proposed in which in a tubular device including a tubular container such as a capillary in which liquid layers of a dissolving/immobilizing liquid, a washing liquid, an elution liquid and the like and gelled medium layers are alternately stacked, magnetic particles are moved along the longitudinal direction of the container to separate and purify a target substance (Patent Document 2).

PRIOR ART DOCUMENTS

Patent Documents

Patent Document 1: International Publication No. WO 97/44671
Patent Document 2: International Publication No. WO 2012/086243

SUMMARY OF THE INVENTION

Problems to be Solved by the Invention

When a tubular device as described in Patent Document 2 is used, magnetic particles are collected on the inner wall surface of a container in the vicinity of a magnetic force source under the action of a magnetic field, and then follow a change of the magnetic field to move along the longitudinal direction of the container, for example from a liquid layer of a dissolving/immobilizing liquid to a gelled medium layer, and to a liquid layer of a washing liquid. In passage of the magnetic particles through the gelled medium layer, the gelled medium is perforated by the magnetic particles. The holes of the gelled medium layer are closed under the self-recovery action by the restoring force of the gel, and therefore inflow of the liquid between two liquid layers separated from each other by the gelled medium layer is suppressed. However, when a tubular container having a large diameter is used, there may be the problem that holes formed in a gelled medium layer have a large size, and thus before the holes of the gelled medium layer are closed, a dissolving/immobilizing liquid flowing into the holes passes through the gelled medium layer together with magnetic particles, and enter a liquid layer of a washing liquid.

In view of the above-mentioned situations, an object of the present invention is to provide a magnetic particle manipulation device, which includes a tubular container in which gelled medium layers and liquid layers are alternately stacked, the device being capable of causing magnetic particles to move and pass through the gelled medium layer while preventing ingress of the liquid of a liquid layer before passage of the magnetic particles through the gelled medium layer into a liquid layer after passage of the magnetic particles through the gelled medium layer.

Means for Solving the Problems

The present inventors have thought that by reducing the diameters of holes formed in passage of magnetic particles through a gelled medium layer, the holes of the gelled medium layer can be quickly closed, so that ingress of the liquid between two liquid layers separated from each other by the gelled medium layer can be suppressed. As a method for reducing the diameters of the holes of the gelled medium layer, mention may be made of a method in which magnetic particles are moved using a tubular container having a small diameter. However, a gelled medium and a liquid are loaded in the container by inserting a needle, and therefore when a tubular container having a small diameter is used, it is difficult to insert the needle into the container and remove the needle from the container. Particularly, if a nozzle at the tip of the needle comes into contact with the inner wall of the container in loading of the gelled medium, the gelled medium may be deposited on the inner wall of the container to cause contamination. When a tubular container having a small diameter is used, the cross-sectional area surrounded by the inner wall surface of the container decreases, so that increase of the amount of magnetic particles is prevented. Thus, use of a tubular container having a small diameter has the problem that the efficiency of separating and purifying a target substance is reduced.

The present inventors have conducted studies, and resultantly found that the diameters of holes formed in the gelled medium layer can be reduced while the cross-sectional area surrounded by the inner wall surface of the container is secured by the followings: at a portion loaded with a gelled medium layer, cross-sectional shape of the inner wall surface of a container is a non-circular shape; and a portion with the cross-sectional shape being a curved shape or an angular shape is set to a magnetic particle movement portion.

The present invention relates to a magnetic particle manipulation device in which gelled medium layer(s) and liquid layers are alternately stacked in a tubular container along a longitudinal direction of the container. In the magnetic particle manipulation device according to the present invention, a magnetic particle movement portion for moving magnetic particles exists along the inner wall surface of the container. The magnetic particle movement portion extends along the longitudinal direction of the container. In a cross section perpendicular to the longitudinal direction of the container at the portion where the gelled medium layer is loaded, a cross-sectional shape of the inner wall surface of the container is non-circular, and a shape of the magnetic particle movement portion is a curved shape or an angular shape.

Where r is a curvature radius of the magnetic particle movement portion at the cross-section, and S is a cross-sectional area surrounded by inner wall surface of the container, r is preferably smaller than $(2S/\pi)^{1/2}$.

Preferably, the inner wall surface of the container has a straight line portion at the cross-section.

In the magnetic particle manipulation device according to the present invention, magnetic particles to be moved in the container may be loaded in the container.

The present invention relates to a kit for preparing the magnetic particle manipulation device.

The present invention relates to a method for manipulating magnetic particles for moving magnetic particles in the magnetic particle manipulation device. In the method according to the present invention, magnetic field manipulation is performed from outside the container so that magnetic particles move along the extending direction of the magnetic particle movement portion.

Effects of the Invention

In a magnetic particle manipulation device according to the present invention, ingress of a liquid between liquid layers separated from each other by a gelled medium layer. Further, it is possible to reduce the problem that contamination easily occurs in loading of a gelled medium and the problem that the amount of magnetic particles to be loaded in the container is limited.

MODE FOR CARRYING OUT THE INVENTION

[Magnetic Particle Manipulating Device]

Figure 1A:
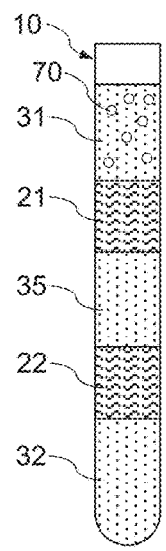
FIGS. 1A to 1C are a schematic sectional views showing one embodiment of magnetic particle manipulating device according to the present invention.
Figure 1B:
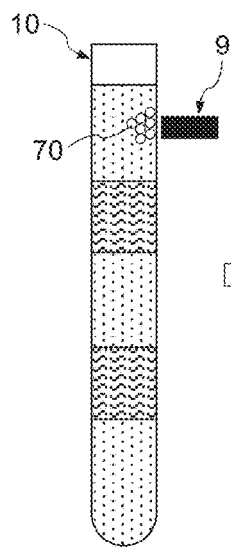
Figure 1C:
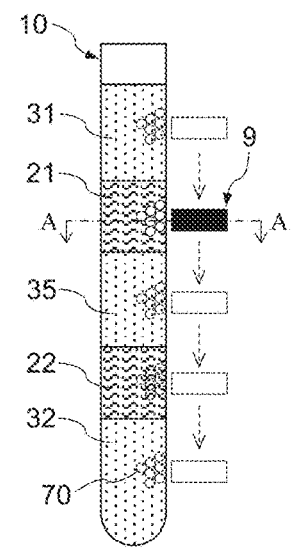

FIGS. 1A to 1C are schematic sectional views showing one embodiment of a magnetic particle manipulation device according to the present invention. As shown in FIG. 1A, the device includes a tubular container 10 in which liquid layers 32, 35 and 31 and gelled medium layers 22 and 21 are alternately stacked from the bottom of the container. The gelled medium is not miscible with liquids in the adjacent liquid layers, and is insoluble or hardly soluble in these liquids.

In FIG. 1A, the liquid layer 31 in the upper part of the container contains a large number of magnetic particles 70. The magnetic particle 70 is capable of selectively immobilizing a target substance such as a nucleic acid or an antigen on the surface or in the inner part of the particle. By dispersing magnetic particles 70 in the liquid layer 31, a target substance contained in the liquid layer 31 is selectively immobilized on the particles 70.

When a magnet 9 as a magnetic force source is brought close to the outer wall surface of the container 10, magnetic particles on which the target substance is immobilized are collected on the inner wall surface of the container 10 in the vicinity of the magnet 9 under the action of a magnetic field as shown in FIG. 1B. When the magnet 9 is moved in the longitudinal direction of the container 10 along the outer wall surface, magnetic particles 70 follow a change of the magnetic field to move along the longitudinal direction of the container 10 to the gelled medium layer 21, to the liquid layer 35, to the gelled medium layer 22, and to the liquid layer 32 as shown in FIG. 1C.

In this specification, a portion for moving magnetic particles in the longitudinal direction of the container along the inner wall surface of the container is referred to as a "magnetic particle movement portion". The magnetic particle manipulation device according to the present invention is characterized in that in a cross section perpendicular to the longitudinal direction of the container at the portion where the gelled medium layer is loaded, the cross-sectional shape of the inner wall surface of the container is non-circular, and the magnetic particle movement portion is a curved shape or an angular shape.

Figure 2:
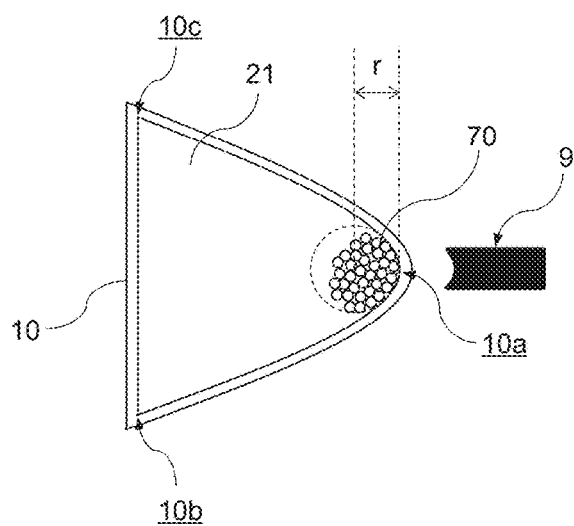
FIG. 2 is a sectional view taken along line A-A in FIG. 1C.

FIG. 2 is a sectional view taken along line A-A in FIG. 1C, and shows a cross-section perpendicular to the longitudinal direction of the container 10 in a portion filled with the gelled medium layer 21. In the description below, the "cross-sectional shape at a plane perpendicular to the longitudinal direction of the container" and the "cross-sectional area at a plane perpendicular to the longitudinal direction of the container" are sometimes abbreviated as a "cross-sectional shape" and a "cross-sectional area", respectively.

The cross-sectional shape of the inner wall surface of the container 10 shown in FIG. 2 is a non-circular shape, and has a curved line portion between a point 10b and a point 10c and a straight line portion between the point 10b and the point 10c. The curved line portion consists of a curved line convexed outward from the container, and has an inflection point 10a. In this specification, a point at which the curved line has the smallest curvature radius, among points on the curved line portion, is referred to as an inflection point.

In this embodiment, $\pi r^2$ is smaller than S, and thus r is smaller than $(S/\pi)^{1/2}$. r is a curvature radius (mm) at the inflection point 10a, and S is a cross-sectional area (mm$^2$) surrounded by the inner wall surface of the container 10.

In this embodiment, the magnet 9 is brought close to the outer wall surface of the container which corresponds to the inflection point 10a in such a manner that the magnet 9 faces the outer wall surface of the container. Consequently, magnetic particles 70 on which a target substance is immobilized are spherically collected in the vicinity of the inflection point 10a so as to follow the curved shape of the inner wall surface. Thereafter, the magnet 9 is moved along the longitudinal direction of the container 10, so that magnetic particles 70 move along the longitudinal direction while being spherically collected in the vicinity of the inflection point 10a. Accordingly, magnetic particles 70 form a rod-like lump, and move in the longitudinal direction of the container 10 to pass through the gelled medium layer 21.

Figure 3:
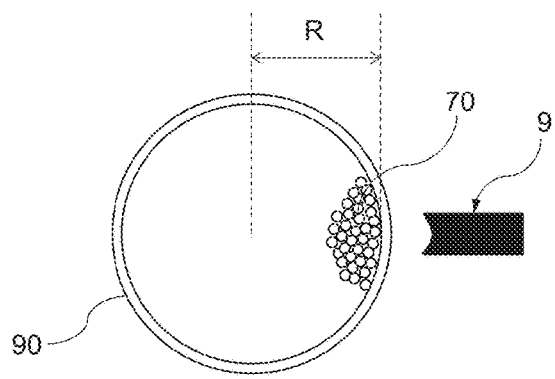
FIG. 3 is a schematic sectional view showing an embodiment in which the cross-sectional shape of the inner wall surface of a container is a circular shape.

FIG. 3 is a schematic sectional view showing a mode in which the cross-sectional shape of the inner wall surface of a container is a circular shape. The cross-sectional shape of the inner wall surface of a container 90 shown in FIG. 3 is a circular shape, and has a cross-sectional area S (mm$^2$) equal to that of the inner wall surface of the container 10 shown in FIG. 2. Where R is a radius (mm) of the inner wall surface of the container 90, S is equal to $\pi R^2$. As mentioned above, $\pi r^2$ is smaller than S in the embodiment of the present invention. Therefore, $\pi r^2$ is smaller than $\pi R^2$, and accordingly r is smaller than R.

When the magnet 9 is brought close to the outer wall surface of the container 90 so as to face the outer wall surface of the container 90, magnetic particles 70 on which the target substance is immobilized are collected so as to follow the curved shape of the inner wall surface of the container 90. Since r is smaller than R, the lump of magnetic particles 70 in FIG. 3 is wider in the circumferential direction as compared to the lump of magnetic particles 70 in FIG. 2. Accordingly, when the magnet 9 is moved along the longitudinal direction of the container 90, magnetic particles 70 form a belt-like lump in the mode of FIG. 3, and move in the longitudinal direction of the container 90 to pass through the gelled medium layer 21.

The gelled medium is perforated due to entry and movement of magnetic particles 70 into the gelled medium layer 21, but the holes of the gelled medium layer are closed under the self-recovery action by the restoring force of the gel. In the embodiment of FIG. 2, the magnetic particle movement portion has a curvature radius r that is smaller than the radius R. By moving magnetic particles 70 as a rod-like lump in the longitudinal direction of the container 10 as shown in FIG. 2, the diameters of the holes of the gelled medium layer 21 can be made smaller as compared to a case where magnetic particles 70 are moved as a belt-like lump as shown in FIG. 3. Accordingly, the holes of the gelled medium layer 21 can be quickly closed, so that ingress of the liquid in the liquid layer 31 into the liquid layer 35 can be prevented.

In the embodiment, the cross-sectional area S of the inner wall surface of the container 10 is larger than $\pi r^2$, and therefore the cross-sectional area of the container can be made larger as compared to a case where the cross-section of the inner wall surface of the container has a circular shape having a radius r. Accordingly, it is possible to reduce the problem that contamination easily occurs in loading of a gelled medium and the problem that the amount of magnetic particles to be loaded into the container cannot be increased.

Hereinafter, using the container having the same cross-sectional shape as in FIG. 2 as an example, the following two cases will be compared: a case where a magnet is disposed so as to face the outer wall surface of a container which corresponds to an inflection point of the inner wall surface of the container; and a case where a magnet is disposed so as to face the outer wall surface of the container which corresponds to a straight line portion of the inner wall surface of the container.

Figure 4A:
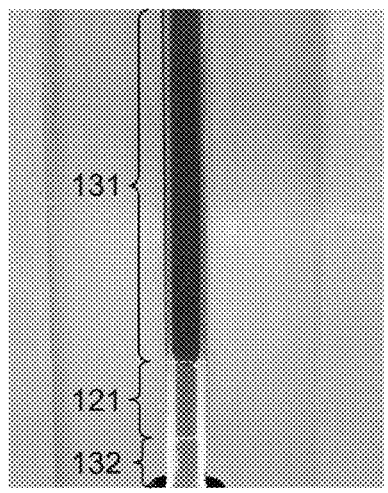
FIGS. 4A to 4C show pictures of an observed state in which a magnetic particle passes through a gelled medium layer when a magnet is disposed so as to face the outer wall surface of a container which corresponds to an inflection point of the inner wall surface of the container.
Figure 4B:
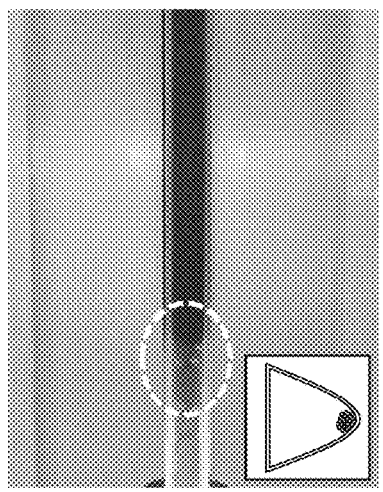
Figure 4C:
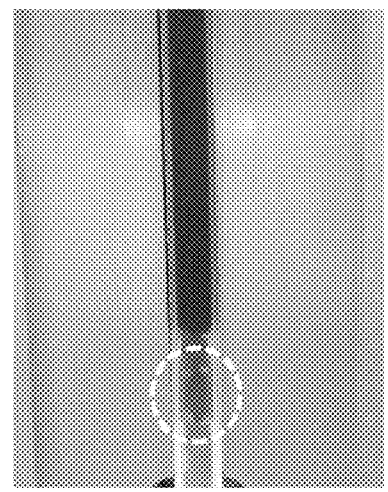

FIGS. 4A to 4C are pictures of an observed state in which a magnetic particle passes through a gelled medium layer when a magnet is disposed so as to face the outer wall surface of a container which corresponds to an inflection point of the inner wall surface of the container. As shown in FIG. 4A, a second water layer 132 as a liquid layer, a gelled medium layer 121, and a first water layer 131 as a liquid layer are disposed in this order from the bottom of the container (lower side on the drawing sheet) in a tubular container. The first water layer 131 is loaded with magnetic particles. Water in the first water layer 131 is stained, and water in the second water layer 132 is colorless. When the magnet is moved along the longitudinal direction of the container, magnetic particles loaded into the first water layer 131 form a rod-like lump and enter the gelled medium layer 121 so as to follow the movement of the magnet as shown in FIG. 4B. When the magnetic particles enters into the gelled medium layer 121, rod-like holes are formed in the gelled medium layer 121 by magnetic particles, and a part of water flows into the holes from the first water layer 131. However, in the gelled medium layer 121, the holes are quickly closed when magnetic particles pass through the gelled medium layer 121, and therefore only a slight amount of water flows into the gelled medium layer 121 from the first water layer 131. Thereafter, the second water layer 132 is not stained by inflow from the first water layer 131 even after magnetic particles pass through the gelled medium layer 121 as shown in FIG. 4C. This result shows that ingress of water from the first water layer 131 into the second water layer 132 is prevented because the holes of the gelled medium layer 121 are quickly closed.

Figure 5A:
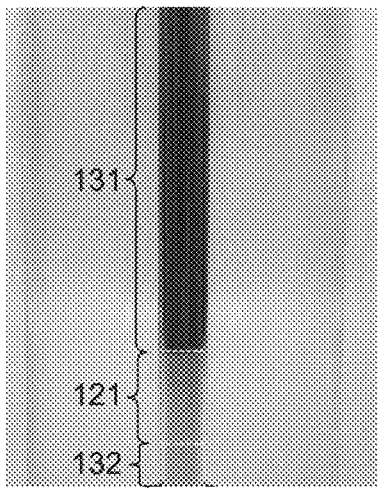
FIGS. 5A to 5C show pictures of an observed state in which a magnetic particle passes through a gelled medium layer when a magnet is disposed so as to face the outer wall surface of a container which corresponds to a straight line portion on the inner wall surface of the container.
Figure 5B:
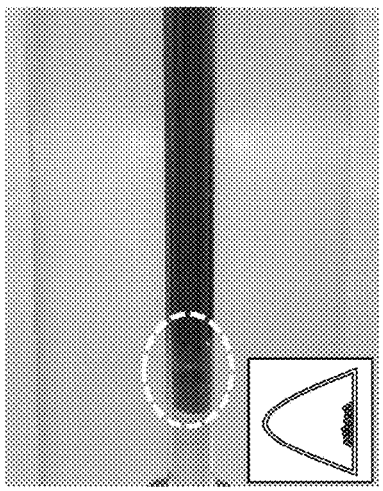
Figure 5C:
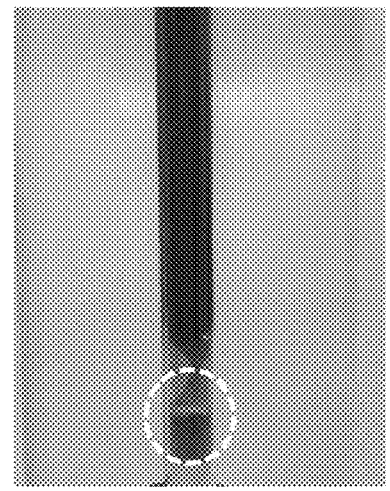

FIGS. 5A to 5C are pictures of an observed state in which a magnetic particle passes through a gelled medium layer when a magnet is disposed so as to face the outer wall surface of a container which corresponds to a straight line portion of the inner wall surface of the container. The case in FIGS. 5A to 5C is the same as in FIGS. 4A to 4C except that a magnet is disposed so as to face the outer wall surface of the container which corresponds to a straight line portion constituting the inner wall surface of the container. When the magnet is moved along the longitudinal direction of the container, magnetic particles loaded into the first water layer 131 form a belt-like lump and enter the gelled medium layer 121 so as to follow the movement of the magnet as shown in FIG. 5B. When the magnetic particles enters into the gelled medium layer 121, belt-like holes are formed in the gelled medium layer 121 by magnetic particles, and a part of water flows into the holes from the first water layer 131. Unlike the case in FIG. 4B, the holes of the gelled medium layer 121 are not immediately closed, and thus water flows into the gelled medium layer 121. Thereafter, the second water layer 132 is stained by inflow from the first water layer 131 after magnetic particles pass through the gelled medium layer 121 as shown in FIG. 5C. This result shows that because the holes of the gelled medium layer 121 are hardly closed, a part of water from the first water layer 131 enters the second water layer 132 before the holes of the gelled medium layer 121 are closed.

From the above results, it is confirmed that when magnetic particles are collected on a magnetic particle movement portion having a curved shape, and moved in the longitudinal direction of a container as a rod-like lump, the diameters of holes formed in the gelled medium layer can be reduced, so that ingress of a liquid between liquid layers separated from each other by the gelled medium layer can be prevented.

An example in which the cross-sectional shape of the magnetic particle movement portion is a curved shape is explained along with an embodiment shown in FIG. 2. The cross-sectional shape of the magnetic particle movement portion may be an angular shape. For example, in FIG. 2, the point 10b or the point 10c may be set to a magnetic particle movement portion.

It should be noted that when the cross-sectional shape of the magnetic particle movement portion is an angular shape like the shape of the point 10b or the point 10c, friction with magnetic particles increases, so that movement of magnetic particles is hindered, and therefore magnetic particles easily clog the magnetic particle movement portion. Accordingly, the cross-sectional shape of the magnetic particle movement portion is preferably a curved shape.

When the cross-sectional shape of the magnetic particle movement portion is a curved shape, the magnetic particle movement portion may be a portion in which $\pi r^2$ is smaller than S, i.e., r is smaller than $(S/\pi)^{1/2}$, where r is a curvature radius of the inner wall surface of the container, and S is a cross-sectional area surrounded by the inner wall surface of the container. The magnetic particle movement portion is preferably one having the smallest curvature radius like the inflection point 10a shown in FIG. 2.

When the cross-sectional shape of the inner wall surface of the container has a curved line portion and a straight line portion, the curved line portion may consist of a circular arc having no inflection point. When the curved line portion consists of a circular arc, every point on the circular arc shape has a certain curvature radius r. In this case, the magnetic particle movement portion may be any portion of the curved line portion in which $\pi r^2$ is smaller than S, i.e., r is smaller than $(S/\pi)^{1/2}$.

When the cross-sectional shape of the inner wall surface of the container has a curved line portion and a straight line portion, the cross-sectional shape is not limited to the shape shown in FIG. 2. The cross-sectional shape of the inner wall surface of the container may have a plurality of straight line portions as in a container 110 shown in FIG. 6A or a container 113 shown in FIG. 6D, or may have a plurality of curved line portions as in a container 111 shown in FIG. 6B. The cross-sectional shape of the inner wall surface of the container may be a polygonal shape having rounded corner portions as in a container 112 shown in FIG. 6C.

Figure 6A:
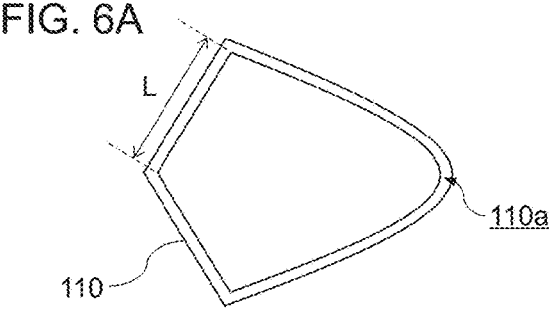
FIGS. 6A to 6D are schematic sectional views each showing an embodiment of a container in which the cross-sectional shape of the inner wall surface has a curved line portion and a straight line portion.
Figure 6B:
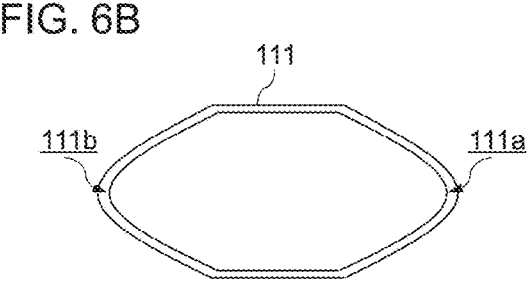
Figure 6C:
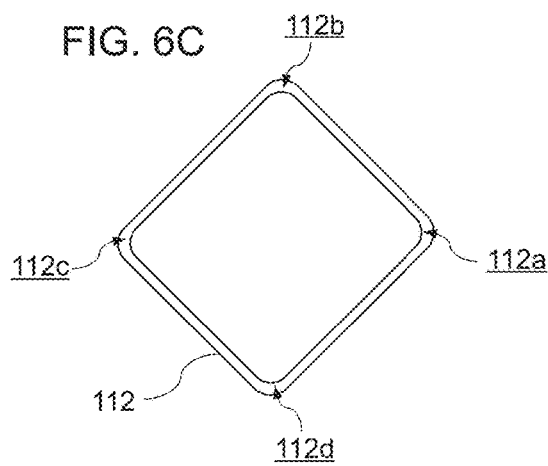
Figure 6D:
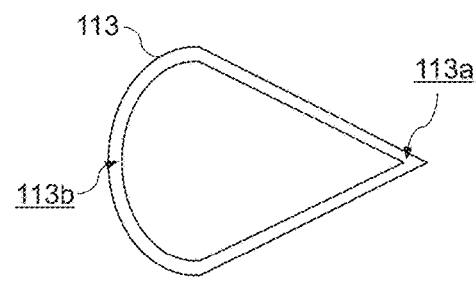

In FIGS. 6A to 6C, inflection points 110a, 111a, 111b and 112a to 112d may be each set to a magnetic particle movement portion as a magnetic particle movement portion having a curved shape. When the curvature radius of an inflection point 113b is large as in FIG. 6D, a point 113a may be set to a magnetic particle movement portion as a magnetic particle movement portion having an angular shape.

The cross-sectional shape of the inner wall surface of the container is not limited to a shape having a curved line portion and a straight line portion, and may be a shape having only a curved line portion, or a shape having only a straight line shape.

Figure 7:
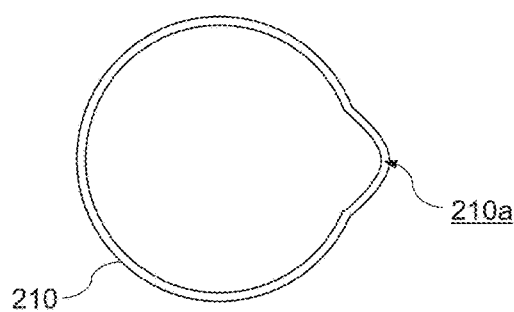
FIG. 7 is a schematic sectional view showing an embodiment of a container in which the cross-sectional shape of the inner wall surface has only a curved line portion.

When the cross-sectional shape of the inner wall surface of the container has only a curved line portion, the cross-sectional shape may be a shape in which a curved line having an inflection point 210a is combined with a circular arc as in a container 210 shown in FIG. 7. Alternatively, the cross-sectional shape of the inner wall surface of the container may be a shape in which curved lines having inflection points different in curvature radius are combined, or a shape in which circular arcs having different radii are combined.

Figure 8:
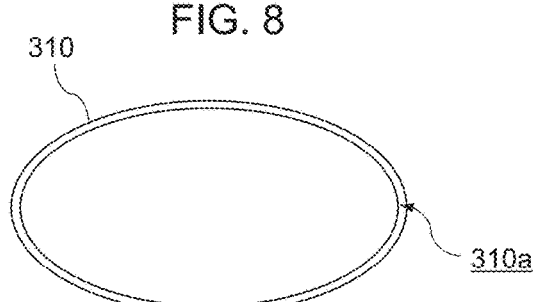
FIG. 8 is a schematic sectional view showing an embodiment of a container in which the cross-sectional shape of the inner wall surface is an elliptic shape.

When the cross-sectional shape of the inner wall surface of the container has only a curved line portion, the cross-sectional shape may be an elliptic shape as in a container 310 shown in FIG. 8.

As aforementioned, the magnetic particle movement portion is preferably a portion in which r is smaller than $(S/\pi)^{1/2}$, and the magnetic particle movement portion is more preferably a portion having the smallest curvature radius, when the cross-sectional shape of the magnetic particle movement portion is a curved shape. For example, in FIG. 7, the magnetic particle movement portion is preferably an inflection point 210a. When the cross-sectional shape of the inner wall surface of the container is an elliptic shape, the curved line has the smallest curvature radius at an inflection point where the curved line crosses the major axis. Accordingly, in FIG. 8, the magnetic particle movement portion is preferably an inflection point 310a.

When the cross-sectional shape of the inner wall surface of the container has only a straight line portion, the cross-sectional shape may be a polygon having any shape.

When the cross-sectional shape of the inner wall surface of the container is a polygon, the curvature radius of each corner portion is 0. Therefore, each corner portion may be set to a magnetic particle movement portion having an angular shape. The corner portions may have the same angle or different angles. When the corner portions have different angles, the magnetic particle movement portion is preferably a portion having the smallest angle.

Although examples in which the cross-sectional shape of the inner wall surface of the container is line-symmetric is explained along with embodiments shown in FIGS. 2 and 6 to 8, the cross-sectional shape of the inner wall of the container is not required to be symmetric as long as it has a magnetic particle movement portion.

As described above, when the cross-sectional shape of the magnetic particle movement portion is an angular shape, friction with magnetic particles increases so that movement of magnetic particles is hindered, and therefore magnetic particles easily clog the magnetic particle movement portion. Accordingly, the cross-sectional shape of the magnetic particle movement portion is preferably a curved shape.

When the inner wall surface of the container has a straight line portion, the curvature radius of the magnetic particle movement portion can be made smaller as compared to a case where the inner wall surface of the container has no straight line portion as long as there is no difference in cross-sectional area. When the outer wall surface of the container which corresponds to the straight line portion is made to face a container pressing portion in movement of magnetic particles by use of an apparatus for manipulating magnetic particles as described later, it is easy to press the container.

In view of the above, it is more preferred that the cross-sectional shape of the inner wall surface of the container has a straight line portion and a magnetic particle movement portion having a curved shape as shown in FIG. 2.

When the cross-sectional shape of the magnetic particle movement portion is a curved shape, the curvature radius r (mm) of the magnetic particle movement portion is preferably 0.5 mm to 10 mm, more preferably 1.5 mm to 5.5 mm.

At least in a portion loaded with the gelled medium layer, the cross-sectional area S ($mm^2$) of the inner wall surface of the container is preferably 0.2 $mm^2$ to 80 $mm^2$, more preferably 1.5 $mm^2$ to 25 $mm^2$.

Where r is a curvature radius (mm) of the magnetic particle movement portion, and S is a cross-sectional area ($mm^2$) surrounded by the inner wall surface of the container, r is preferably smaller than $(S/\pi)^{1/2}$, and r may be smaller than $0.5 \times (S/\pi)^{1/2}$. r is equal to or larger than 0.

r may be smaller than $(2S/\pi)^{1/2}$, depending on the cross-sectional shape of the inner surface of the container. For example, when the cross-sectional shape of the inner wall surface of the container as in a container 410 shown in FIG. 9, the cross sectional area of the inner wall surface of the container is expressed by the formula: $S=\pi n R_1^2/2$ where $R_1$ is a short diameter, and $nR_1$ (n is a coefficient larger than 1) is a long diameter. Here, it is preferred that the curvature radius r of the magnetic particle movement portion satisfies the relationship of $r<R_1$, i.e., $r<(2S/\pi n)^{1/2}$. Since n is larger than 1, r is preferably smaller than $(2S/\pi)^{1/2}$. The curvature radius $r_1$ at an inflection point 410a where the curved line crosses the long axis is expressed by the formula: $r_1=R_1/n$. Since n is larger than 1, $r_1$ is smaller than $R_1$.

Figure 9:
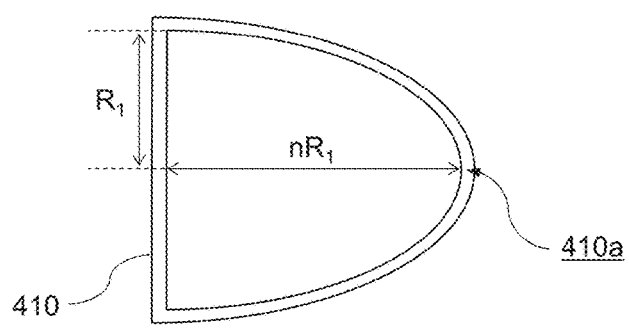
FIG. 9 is a schematic sectional view showing an embodiment of a container in which the cross-sectional shape of the inner wall surface is a semi-elliptic shape.

In FIG. 9, a case where the cross-sectional shape of the inner wall surface of the container is a semi-elliptic shape is explained. When the cross-sectional shape of the inner wall surface of the container consists of a curved line portion and one straight line portion (particularly by a curved line portion having one inflection point, and one straight line portion) including the case in FIG. 2, r is preferably smaller than $(2S/\pi)^{1/2}$. When the cross-sectional shape of the inner wall surface of the container consists of a curved line portion and two straight line portions (particularly by a curved line portion having one inflection point, and two straight line portions) as shown in FIG. 6A, the curvature radius r of the magnetic particle movement portion is preferably smaller than the length L of the straight line portion.

In the magnetic particle manipulation device according to the present invention, it suffices that at least in a portion loaded with the gelled medium layer, the cross-sectional shape of the inner wall surface of the container is a non-circular shape, and the cross-sectional shape of the magnetic particle movement portion is a curved shape or an angular shape. In particular, it is preferred that in a region where magnetic particles move, the cross-sectional shape of the inner wall surface of the container is a non-circular shape, and the cross-sectional shape of the magnetic particle movement portion is a curved shape or an angular shape, and it is more preferred that in the whole of the container in the longitudinal direction, the cross-sectional shape of the inner wall surface of the container is a non-circular shape, and the cross-sectional shape of the magnetic particle movement portion is a curved shape or an angular shape.

The wall thickness of the container is not particularly limited as long as the cross-sectional shape of the inner wall surface of the container is the above-mentioned shape. When the wall thickness of the container is constant on a side on which the container faces a magnet, the distance between the magnet and the inner wall surface of the container can be kept constant, and therefore magnetic particles can be smoothly moved. Accordingly, on a side on which the container faces the magnet, the wall thickness of the container is constant preferably at least in a portion loaded with the gel medium layer, more preferably in the whole portion. It is especially preferred that the wall thickness is constant in the whole of the container in the longitudinal direction.

The container is not necessarily required to have a straight-tubular shape, and the container may have a portion with a large diameter and a portion with a small diameter when viewed along the longitudinal direction of the tube.

The length of the container is not particularly limited, and may be about 50 mm to 200 mm as one example. The cross-sectional area and the length of the inner wall of the container may be appropriately selected according to the amount of a substance to be treated, the amount of magnetic particles, and so on.

The material of the container is not particularly limited as long as magnetic particles can be moved in the container, and a liquid and a gelled medium can be held. A magnetically permeable material such as a plastic is preferred for moving magnetic particles in the container by magnetic field manipulation from outside the container. Examples of the plastic include resin materials such as polyolefins such as polypropylene and polyethylene, fluorine-based resins such as tetrafluoroethylene, polyvinyl chloride, polystyrene, polycarbonates and cyclic polyolefins. In addition to these, ceramic, glass, silicone, metals and so on may also be used as the material of the container. The inner wall surface of the container may be coated with a fluorine-based resin, silicone or the like for improving the water repellency thereof.

In the case where optical measurement of an absorbance, a fluorescence, a chemiluminescence, a bioluminescence, a change in refractive index, or the like is performed during or after manipulation of particles, or photo irradiation is performed, a container permeable to light is preferably used. In addition, the use of a container permeable to light is preferred because the state of particle manipulation in the container can be visually observed. On the other hand, in the case where it is necessary to shield the liquid, magnetic particles and so on from light, a container impermeable to light, such as one made of a metal or the like, is preferably used. A container having a light-permeable part and a light-shielding part may also be employed depending on the use purpose or the like.

Other configurations of the magnetic particle manipulation device according to the present invention are not particularly limited as long as gelled medium layers and liquid layers are alternately stacked in a tubular container, and the container has the above-mentioned shape.

The immobilization method is not particularly limited, and various kinds of known immobilization mechanisms such as physical adsorption and chemical adsorption are applicable. A target substance is immobilized on the surfaces of particles or in particles by various intermolecular forces such as a Van der Waals force, a hydrogen bond, a hydrophobic interaction, an interionic interaction and π-π stacking.

The particle size of the magnetic particle is preferably 1 mm or less, more preferably 0.1 μm to 500 μm. The shape of the particle is desired to be a spherical shape with the particle size being uniform, but may be an irregular shape, and have a measurable particle size distribution as long as particle manipulation is possible. The constituent of the particle may be a single substance, or may include a plurality of components.

The magnetic particle may be composed only of a magnetic substance. Magnetic particle subjected to a coating on the surface for selectively immobilizing a target substance is preferably used. Examples of the magnetic substance include iron, cobalt, nickel, and compounds, oxides and alloys thereof. Specific examples include magnetite ($Fe_3O_4$), hematite ($Fe_2O_3$ or $\alpha Fe_2O_3$), maghemite ($\gamma Fe_2O_3$), titanomagnetite ($xFe_2TiO_4.(1-x)Fe_3O_4$), ilmenohematite ($xFeTiO_3.(1-x)Fe_2O_3$), pyrrhotite ($Fe_{1-x}S$ (x=0 to 0.13) . . . $Fe_7S_8$ (x≈0.13)), greigite ($Fe_3S_4$), geothite ($\alpha FeOOH$), chromium oxide ($CrO_2$), permalloy, alconi magnets, stainless steel, samarium magnets, neodymium magnets and barium magnets.

Examples of the target substance that is selectively immobilized to the magnetic particles include organism-derived substances such as nucleic acids, proteins, sugars, lipids, antibodies, receptors, antigens and ligands, and cells themselves. When the target substance is an organism-derived substance, the target substance may be immobilized on particles, or a substance on the surfaces of particles by molecular recognition or the like. For example, when the target substance is a nucleic acid, magnetic particles with silica surface coating are preferably used. When the target substance is an antibody (e.g., labeled antibody), a receptor, an antigen a ligand or the like, the target substance can be selectively immobilized on the surfaces of particles by means of amino groups, carboxyl groups, epoxy groups, avidin, biotin, digoxigenin, protein A, protein G or the like on the surfaces of particles. Commercial products such as Dynabeads (registered trademark) available from Life Technologies, Inc. and MagExtractor (registered trademark) available from TOYOBO CO., LTD. may also be used as the magnetic particle capable of selectively immobilizing a specific target substance.

In FIGS. 1A to 1C, magnetic particles 70 are dispersed in the liquid layer 35 and the liquid layer 31, so that the magnetic particles are brought into contact with the liquid in the liquid layer to carry out operations such as immobilization of a target substance on magnetic particles, washing operation for removing contaminants deposited on the surfaces of magnetic particles, reaction of the target substance immobilized on magnetic particles, and elution of the target substance immobilized on magnetic particles into the liquid.

For example, when a nucleic acid is to be separated and extracted using magnetic particles coated with silica, magnetic particles 70 are dispersed in a liquid sample 31 containing a nucleic acid extraction liquid and a nucleic acid, the nucleic acid is immobilized on the surfaces of magnetic particles 70, and magnetic particles 70 are then moved into the washing liquid 35. Magnetic particles 70 are dispersed in the washing liquid 35 to remove contaminant proteins etc. deposited on the surfaces of the particles, and magnetic particles 70 are then moved into the nucleic acid elution liquid 32. By dispersing magnetic particles 70 in the nucleic acid elution liquid 32, the nucleic acid immobilized on the surfaces of the particles can be recovered in the nucleic acid elution liquid 32. In FIGS. 1A to 1C, one liquid layer 35 as a washing liquid is loaded in the container 10, but two liquid layers or three or more liquid layers may be loaded in the container as the washing liquid. The washing liquid may be omitted as long as undesired hindrance in the purpose of separation and application does not occur.

When the substance to be selectively immobilized on magnetic particles is an antigen, the antigen contained in the liquid layer 31 as a first medium layer is immobilized on the surfaces of magnetic particles 70 coated with a molecule capable of selectively immobilizing antigens such as protein G and protein A. The magnetic particles are dispersed in the liquid layer 35 to carry out washing for removing contaminants deposited on the surfaces of the particles. By dispersing the magnetic particles in the liquid layer 32 as a second medium layer, antigen antibody reaction of the antigen immobilized on the surfaces of the particles and an antibody in the liquid layer 32, release and elution of a target substance into the liquid layer 32, and so on may be carry out.

The above-mentioned method for manipulating particles can be carried out in a closed system because it is not necessary to generate a liquid flow with a pipette etc. When a liquid, a gelled medium and magnetic particles are loaded in the container and the container is sealed, contamination from outside can be prevented. Accordingly, the method for manipulating particles is particularly useful in a case where an easily decomposable target substance such as RNA is immobilized on magnetic particles, a liquid that easily reacts with oxygen etc. in air is used, or the like. For bringing the container into a closed system, the opening of the container can be heat-sealed, or the container can be sealed using an appropriate sealing means. In the case where it is necessary that manipulated particles and a liquid after elution of a target substance be taken out to the outside of the container, it is preferred to detachably seal the opening using a resin stopper or the like. As in the device shown in FIGS. 1A to 1C, the liquid may be sealed in the container by bringing a gel layer etc. into contact with the liquid.

The liquid loaded in the container provides a field for chemical operations such as extraction, purification, reaction, separation, detection and analysis of a target substance immobilized on the surfaces of particles. Although the type of the liquid is not particularly limited, a liquid that does not dissolve the gelled medium is preferred. Accordingly, as the liquid, a water-based liquid such as an aqueous solution, or a mixed solution of water and an organic solvent is preferably used. The liquid can serve as a mere medium for these chemical operations, and may also be directly involved in the chemical operation, or contain as a component a compound which is involved in the operation. Examples of the substance contained in the liquid may include substances that react with a reactive substance immobilized on magnetic particles, substances that further react with a substance immobilized on the surfaces of magnetic particles by the reaction, reaction reagents, fluorescent substances, various kinds of buffers, surfactants, salts, various kinds of other auxiliary agents, and organic solvents such as alcohols. Water-based liquid can be provided in any form such as water, an aqueous solution or an aqueous suspension.

When a target substance contained in a liquid sample is immobilized on the surfaces of magnetic particles, the liquid may contain a variety of contaminants in addition to the target substance to be immobilized on the surfaces of the magnet particles. The liquid sample may include nucleic acid containing materials such as animal and plant tissues, body fluids and excretions; or nucleic acid inclusion bodies such as cells, protozoa, fungi, bacteria and viruses. The body fluids include blood, spinal fluids, saliva and milk. The excretions include feces, urine and sweat. The cells include leukocytes and blood platelets in blood, exfoliated cells of mucosal cells such as oral cells, and leukocytes in saliva.

A liquid sample containing a target substance such as a nucleic acid, an antigen or an antibody may be prepared in the form of, for example, a cell suspension, a homogenate, or a mixed liquid with a cell lysate. When a target substance contained in an organism-derived sample such as blood is immobilized on the surfaces of the particles, the liquid sample is a mixture of the organism-derived sample such as blood and a cell lysate (nucleic acid extraction liquid) for extracting the target substance from the sample. The cell lysate contains a component capable of dissolving cells, such as a chaotropic substance or a surfactant.

Examples of cell lysate (nucleic acid extraction liquid) to be used for extracting a nucleic acid include buffers containing a chaotropic substance, a chelating agent such as EDTA, tris-hydrochloric acid or the like. The cell lysate may contain a surfactant such as TritonX-100. Examples of the chaotropic substance include guanidine hydrochloride, guanidine isothiocyanate, potassium iodide and urea. The cell lysate may contain, in addition to the above-mentioned components, proteolytic enzymes such as protease K, various kinds of buffers, salts, various kinds of other auxiliary agents, and organic solvents such as alcohols.

The washing liquid is not limited as long as it ensures that components other than a nucleic acid (e.g., proteins, sugars and so on), which are contained in a sample, and a reagent or the like used for a treatment such as nucleic acid extraction can be released into the washing liquid. Examples of the washing liquid include high-salt-concentration aqueous solutions such as those of sodium chloride, potassium chloride and ammonium sulfate, and aqueous alcohol solutions such as those of ethanol and isopropanol.

As the nucleic acid elution liquid, water, or a buffer containing a low-concentration salt can be used. Specifically, a tris-buffer, a phosphate buffer, distilled water or the like can be used, and a 5 to 20 mM tris-buffer adjusted to have a pH of 7 to 9 is generally used. By dispersing magnetic particles, on which a nucleic acid is immobilized, in an elution liquid, the nucleic acid can be released and eluted in a nucleic acid elution liquid. The recovered nucleic acid can be provided for analysis, reaction and so on after being subjected to operations such as concentration and drying as necessary.

The gelled medium to be loaded into the container may be in the form of a gel or a paste before manipulation of particles. The gelled medium is preferably a substance which is insoluble or hardly soluble in liquids in the adjacent liquid layers, and chemically inactive. Here, the term "insoluble or hardly soluble in a liquid" means that the solubility in a liquid at 25° C. is 100 ppm or less. The chemically inactive substance refers to a substance which does not chemically affect liquid layers, magnetic particles and a substance immobilized on the magnetic particles in contact with the liquid layer and manipulation of magnetic particles (i.e. manipulation for moving magnetic particles in the gelled medium).

The material, composition and so on of the gelled medium are not particularly limited, and the gelled medium may be a physical gel or a chemical gel. For example, as described in WO 2012/086243, a liquid substance insoluble or hardly soluble in water is heated, a gelling agent is added to the heated liquid substance, and fully dissolved in the liquid substance, and the solution is cooled to a temperature equal to or lower than a sol-gel transition temperature to form a physical gel.

A gelled medium and a liquid may be loaded in a container by an appropriate method. In the case where a tubular container is used, it is preferred that the opening at one end of the container is sealed prior to loading, and a gelled medium and a liquid are sequentially loaded through the opening at the other end. As aforementioned, in the magnetic particle manipulation device according to the present invention, the cross-sectional area of the inner wall surface of the container can be made wider as compared to a case where the cross-section of the inner wall surface of the container has a circular shape, and therefore it is possible to reduce the problem that contamination easily occurs in loading of a gelled medium.

The volume of each of the gelled medium and the liquid loaded in the container can be appropriately set according to the amount of magnetic particles to be manipulated, the type of manipulation or the like. In the case where a plurality of gelled media layers and liquid layers are provided in the container, the volumes of the layers may be the same or different. The thickness of each layer can be appropriately set, and is preferably, for example, about 2 mm to 20 mm in consideration of manipulability or the like.

The magnetic particle manipulation device according to the present invention can be prepared by loading a gelled medium and a liquid into a tubular container having the above-mentioned shape. The liquid to be loaded into the container is, for example, a liquid capable of dissolving cells, such as a nucleic acid extraction liquid. The liquid may contain an alcohol etc. Magnetic particles are loaded into the container in use of the device. The device may be prepared in a state in which a liquid such as a nucleic acid extraction liquid and magnetic particles coexist beforehand.

[Kit for Preparation of Magnetic Particle Manipulation Device]

A gelled medium, a liquid and so on may be provided independently of a container. The container may be loaded with the gelled medium and the liquid immediately before manipulation of particles, or at a sufficient time before manipulation of particles. When the gelled medium is insoluble or hardly soluble in the liquid, reaction or absorption hardly occurs between the gelled medium and the liquid even after elapse of a long time after loading.

Magnetic particles may be provided as one constituent member of a kit for preparing the device. Magnetic particles may be provided as one constituent member of a kit in a state in which the magnetic particles exist in the liquid.

The amount of magnetic particles which are contained in the device or the kit is appropriately determined according to the type of intended chemical operation, the volume of each liquid layer, or the like. For example, in the case where a long and narrow capillary having a cross-sectional area of about 2 mm$^2$ to 15 mm$^2$ is used, the suitable amount of magnetic particles is normally in the range of about 10 to 200 μg.

[Apparatus for Manipulating Magnetic Particles]

Figure 10A:
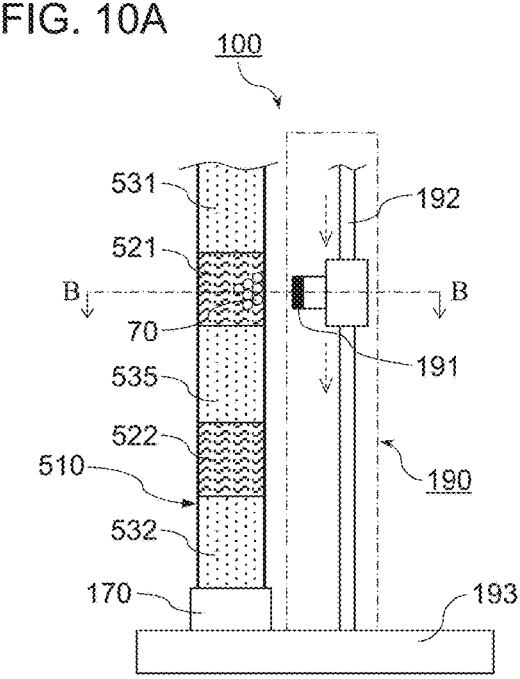
FIGS. 10A and 10B show schematic views showing one embodiment of an apparatus for manipulating magnetic particles according to the present invention.

FIG. 10A is a schematic view showing one embodiment of an apparatus for manipulating magnetic particles in which manipulation of magnetic particles can be automated. An apparatus 100 for magnetic particle manipulation as shown in FIG. 10A includes a container holding unit 170 and a magnetic field applying unit 190.

The magnetic applying unit 190 is configured such that the magnetic field can be changed. The magnetic field applying unit 190 includes a linear guide 192 fixed on a support plate 193, and a permanent magnet 191 slidably attached on the linear guide 192. The method for sliding the permanent magnet 191 is not particularly limited, and the permanent magnet 191 may be slid by driving means such as a motor, or slid manually. Since the permanent magnet 191 can be slid on the linear guide 192, the magnetic field can be changed in a uniaxial direction. In the magnetic particle manipulation apparatus 100, magnetic particles 70 can be moved in a container 510 in the longitudinal direction of the container 510 by moving the permanent magnet 191 in the uniaxial direction.

The container holding unit 170 is configured such that the container 510 can be held. In the container 510, liquid layers 531, 535 and 532 and gelled medium layers 521 and 522 are alternately stacked, and magnetic particles 70 are loaded in the container 510. The container 510 is detachably held in the container holding unit 170.

Figure 10B:
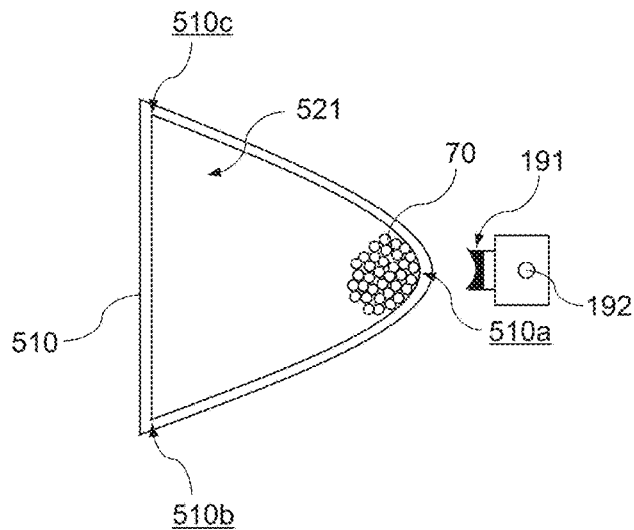

FIG. 10B is a sectional view taken along line B-B in FIG. 10A. As shown in FIG. 10B, the container 510 has the same cross-sectional shape as that of the container 10 shown in FIG. 2. Specifically, the cross-sectional shape of the inner wall surface of the container 510 is a non-circular shape, and has a curved line portion between a point 510$b$ and a point 510$c$ and a straight line portion between the point 510$b$ and the point 510$c$. The curved line portion consists of a curved line convexed outward from the container, and has an inflection point 510$a$.

The container 510 is held by the container holding unit 170 in such a manner that the outer wall surface corresponding to the inflection point 510$a$ faces the permanent magnet 191. Accordingly, magnetic particles 70 are spherically collected in the vicinity of the inflection point 510$a$ so as to follow the curved shape of the inner wall surface. In the container 510, the inflection point 510$a$ is set to a magnetic particle movement portion.

As shown in FIG. 10A, the permanent magnet 191 is moved along the linear guide 192, so that magnetic particles 70 attracted to the permanent magnet 191 move along the longitudinal direction while being spherically collected in the vicinity of the inflection point 510$a$. Accordingly, magnetic particles 70 form a rod-like lump, and move along the longitudinal direction of the container 510 to pass through the liquid layer 531 and then the gelled medium layer 521 to the liquid layer 535.

By using the above-mentioned apparatus for manipulating magnetic particles, manipulation of magnetic particles can be automated in the foregoing magnetic particle manipulation device.

The apparatus for manipulating magnetic particles is not limited to the above-described configuration, and various configurations can be employed.

In FIG. 10A, the permanent magnet 191 is moved in only one direction (downward), but the permanent magnet 191 may be moved in a reciprocative manner in two directions (upward and downward).

An electromagnet as well as a permanent magnet may be used as a magnetic force source of the magnetic field applying unit. The magnetic field applying unit may have a plurality of magnetic force sources.

The direction in which the container is held is not particularly limited, and instead of holding the container in such a manner that the longitudinal direction of the container is vertical, the container may be held, for example, in such a manner that the longitudinal direction of the container is horizontal, or the longitudinal direction of the container is oblique.

The method for changing the magnetic field along the longitudinal direction of the container is not limited to a configuration shown in FIG. 10A, in which the magnetic field applying unit has a moving mechanism such as a linear guide for moving the magnetic force source in a uniaxial direction. For example, a configuration in which the container holding unit has a moving mechanism such as a linear guide may be employed so that the container holding unit is moved in a uniaxial direction. In other words, the container holding unit and the magnetic field applying unit may have a moving mechanism capable of relatively moving the magnetic force source in a uniaxial direction with respect to the container holding unit. Both the container holding unit and the magnetic field applying unit may have the moving mechanism so that both the magnetic force source and the container holding unit move.

DESCRIPTION OF REFERENCE SIGNS 10, 90, 110, 111, 112, 113, 210, 310, 410, 510: container
10$a$, 110$a$, 111$a$, 112$a$, 113$a$, 210$a$, 310$a$, 410$a$, 510$a$: magnetic particle movement portion
70: magnetic particle
9: magnet (magnetic force source)
21, 22, 121, 521, 522: gelled medium (layer)
31, 32, 35, 131, 132, 531, 532, 535: liquid (layer)
100: magnetic particle manipulation apparatus
170: container holding unit
190: magnetic applying unit

The invention claimed is:

1. A magnetic particle manipulation device comprising:
a container;
a magnet; and
an upper liquid layer, a gelled medium layer, and a lower liquid layer alternately stacked within the container in this order along a longitudinal direction of the container, wherein
an inner wall surface of the container includes a portion configured to move magnetic particles, the portion configured to move the magnetic particles extending along the longitudinal direction of the container at the gelled medium layer, and
in a cross section perpendicular to the longitudinal direction of the container at the portion configured to move the magnetic particles, a cross-sectional shape of the inner wall surface of the container is a non-circular curved shape including an inflection point or an angular shape, and
the magnet faces an outer wall surface of the container at the inflection point or the angular shape of the portion configured to move the magnetic particles, and the magnet is configured to be moved in the longitudinal direction along the outer wall surface of the container.

2. The magnetic particle manipulation device according to claim 1, wherein $r<(2S/\pi)^{1/2}$ is satisfied in the cross section, where r is a curvature radius of the inner wall surface at the portion configured to move the magnetic particles, and S is a cross-sectional area within the inner wall surface of the container.

3. The magnetic particle manipulation device according to claim 1, wherein the cross-sectional shape of the inner wall surface of the container has a straight line portion.

4. The magnetic particle manipulation device according to claim 1, wherein the magnetic particles to be moved in the container are loaded in the container.

\* \* \* \* \*